United States Patent
Majumder et al.

(10) Patent No.: US 11,446,222 B2
(45) Date of Patent: Sep. 20, 2022

(54) COMPOSITION FOR TREATING KERATIN FIBERS COMPRISING AN AMPHOTERIC OR CATIONIC POLYMER AND NEUTRALIZED FATTY ACID

(71) Applicant: L'OREAL, Paris (FR)

(72) Inventors: Suman Majumder, Mumbai (IN); Sagar Agawane, Mumbai (IN); Ankita Mital, Mumbai (IN); Sudhahar Vijayaraghavan, Mumbai (IN); Shilpa Halder Joshi, Mumbai (IN); Maxime De Boni, Mumbai (IN)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/316,972

(22) PCT Filed: Jul. 25, 2017

(86) PCT No.: PCT/EP2017/068798
§ 371 (c)(1),
(2) Date: Jan. 10, 2019

(87) PCT Pub. No.: WO2018/019852
PCT Pub. Date: Feb. 1, 2018

(65) Prior Publication Data
US 2019/0240128 A1 Aug. 8, 2019

(30) Foreign Application Priority Data

Jul. 26, 2016 (IN) .............................. 201631025511

(51) Int. Cl.
| | |
|---|---|
| *A61K 8/22* | (2006.01) |
| *A61K 8/31* | (2006.01) |
| *A61K 8/34* | (2006.01) |
| *A61K 8/36* | (2006.01) |
| *A61K 8/39* | (2006.01) |
| *A61K 8/86* | (2006.01) |
| *A61Q 5/08* | (2006.01) |
| *A61Q 5/10* | (2006.01) |
| *A61K 8/73* | (2006.01) |

(52) U.S. Cl.
CPC ................ *A61K 8/361* (2013.01); *A61K 8/22* (2013.01); *A61K 8/31* (2013.01); *A61K 8/342* (2013.01); *A61K 8/39* (2013.01); *A61K 8/731* (2013.01); *A61K 8/86* (2013.01); *A61Q 5/08* (2013.01); *A61Q 5/10* (2013.01); *A61K 2800/432* (2013.01)

(58) Field of Classification Search
None
See application file for complete search history.

(56) References Cited

U.S. PATENT DOCUMENTS

| | | | | |
|---|---|---|---|---|
| 5,154,847 | A * | 10/1992 | LaPetina ................ | A61K 8/044 424/705 |
| 2004/0133994 | A1* | 7/2004 | Cottard ................ | A61K 8/8176 8/405 |

FOREIGN PATENT DOCUMENTS

| | | | |
|---|---|---|---|
| EP | 1413287 | 4/2004 | |
| EP | 1707190 | 10/2006 | |
| EP | 1891933 | 2/2008 | |
| EP | 2266528 | 12/2010 | |
| WO | 2002058647 | 8/2002 | |
| WO | 2005074873 | 8/2005 | |
| WO | WO-2005074873 A1 * | 8/2005 | ............. A61K 8/342 |
| WO | 2013160360 | 10/2013 | |

OTHER PUBLICATIONS

SciFinder CAS registration listing for "Oleic acid ethanolamide" (Year: 2020).*
CAS Registry listing for "Lauryl alcohol" (Year: 2021).*
CAS Registry listing for "Myristyl alcohol" (Year: 2021).*

* cited by examiner

*Primary Examiner* — Brian Gulledge
(74) *Attorney, Agent, or Firm* — Michael B. Rubin; Rudy J. Ng; Bozicevic, Field & Francis LLP

(57) ABSTRACT

The present invention relates to a composition for dyeing and/or bleaching human keratin fibers, such as the hair, comprising: a) at 0.15% of at least one neutralized fatty acid, please confirm the minimum amount of fatty acid salt in the ready to use composition b) at least one non ionic surfactant, c) at least one non associative polymer chosen from amphoteric polymers, cationic polymers and mixture thereof, d) at least 10% by weight relative to the total weight of the composition, of at least one fatty substance other than fatty acids, e) at least one oxidizing agent, and f) optionally at least one oxidation dye precursor and/or at least one direct dye. The invention also relates to a method for treating human keratin fibres using this composition.

19 Claims, No Drawings

COMPOSITION FOR TREATING KERATIN FIBERS COMPRISING AN AMPHOTERIC OR CATIONIC POLYMER AND NEUTRALIZED FATTY ACID

The present invention relates to a composition comprising a non associative amphoteric or cationic polymer, at least 0.15% of neutralized fatty acid(s), at least one non ionic surfactant, at least 10% of fatty substance(s) other than fatty acids, an oxidizing agent, an alkaline agent, and optionally at least one oxidation dye precursor and/or at least one direct dye.

It is known practice, for the treatment of hair, to use oxidizing compositions, more particularly for dyeing human keratin fibres, and especially the hair, with dyeing compositions containing oxidation dye precursors, generally referred to as oxidation bases. These oxidation bases are colourless or weakly coloured compounds which, in combination with oxidizing products, give rise, by a process of oxidative condensation, to coloured compounds.

The method of oxidation dyeing involves applying, to the keratin fibres, oxidation bases, or a mixture of oxidation bases and couplers, with an oxidizing agent, such as hydrogen peroxide, which is added at the time of use.

Generally speaking, this method is implemented at an alkaline pH, more particularly in the presence of ammonia, and produces a dyeing and, at the same time, a lightening of the fibre that is manifested in practice by the possibility of obtaining an eventual coloration which is lighter than the original colour. Moreover, the lightening of the fibre has the advantageous effect of bringing about a unified colour in the case of depigmented hair, and of emphasizing the colour—that is, making it more visible—in the case of naturally pigmented hair.

It is likewise known practice to dye human keratin fibres by what is called semi-permanent coloration or direct coloration, which employs dyes that are capable of themselves providing a more or less marked modification to the natural colouring of the hair.

These direct dyes may also be used in combination with oxidizing agents, where the desire is to obtain a coloration which is lighter than the original colour of the fibres. Accordingly, these direct dyes may be used in compositions for lightening direct dyeing that are based on hydrogen peroxide and ammonia, or in compositions for oxidation dyeing in association with oxidation bases and/orcouplers.

Furthermore, when a person wishes to bleach their hair, it is also known practice to carry out bleaching using lightening products based on ammonia and hydrogen peroxide.

Accordingly, it is usual to employ alkaline oxidizing compositions that are based on hydrogen peroxide and ammonia for the purpose of colouring and/or bleaching human keratin fibres, and especially the hair.

However, although these conditions of use do prove to be effective, they may give rise to a certain number of annoyances at the time of their use.

In particular, when these compositions are applied to the hair, there is generally a release of ammonia, which can lead to a suffocating odour which is irritating to the eyes, airways and mucous membranes.

Moreover, particularly in persons with a sensitive scalp, the ammonia may give rise to reactions of discomfort, such as redness, itching or pricking.

Finally, ammonia, in combination with the oxidizing agent, may also contribute to damaging the keratin fibres. Indeed, over the long term, the fibres are observed to be or more less degraded and to have a tendency to become lank, dull, fragile and difficult to style.

Accordingly, in order to remedy all of the drawbacks described above, numerous alternatives have already been proposed for the purpose of significantly reducing the levels of ammonia in compositions that are intended for the colouring and/or bleaching of fibres.

To this end, proposals have been made to apply, to the hair, colouring and/or bleaching compositions that comprise a non-volatile organic amine, such as monoethanolamine. Although such compositions do have the advantage of not releasing ammonia while they are being used, they usually give rise to reactions of discomfort, and especially to irritation in people with a sensitive scalp. Furthermore, for equivalent lightening performance, monoethanolamine damages the hair in a way which is greater than that of ammonia.

To improve the hair conditions it has been proposed to use conditioning polymers, such as cationic or amphoteric polymers, but scalp comfort issues can still occur.

There is a need to propose compositions able to improve deposition of such conditioning polymers onto the hair while reducing exposure of the scalp to these ingredients.

The objectives of the present invention is to reduce the unpleasant odours of alkaline compositions, in particular when ammonia is used, generally accompanying the process of colouring and/or for bleaching hair, the discomfort of the scalp (such as irritation, itching for exempla) and the damage to the keratin fibres, while retaining good colouring and/or bleaching properties.

These objectives are achieved with the present invention, which provides a composition for treating keratin fibres, especially for dyeing and/or bleaching human keratin fibers, such as the hair, comprising:

a) at least 0.15% of at least one neutralized fatty acid,
b) at least one non ionic surfactant,
c) at least one non associative polymer chosen from amphoteric polymers, cationic polymers and mixture thereof,
d) at least 10% by weight relative to the total weight of the composition, of at least one fatty substance other than fatty acids,
e) at least one oxidizing agent,
f) at least an alkaline agent, and
g) optionally at least one oxidation dye precursor and/or at least one direct dye.

The invention also relates to a method for treating keratin fibres, especially dyeing and/or bleaching keratin fibres, which includes applying on said fibres the above composition.

The invention also relates to a method for treating keratin fibres, especially dyeing and/or bleaching which includes applying a ready to use composition resulting from the mixture of:

(a) a composition (A) comprising at least an alkaline agent and optionally at least one oxidation dye precursor and/or at least one direct dye,
(b) a composition (B) comprising at least one oxidizing agent,
  at least one of composition A and B comprising:
  at least one non ionic surfactant,
  at least one non associative polymer chosen from amphoteric polymers, cationic polymers and mixture thereof,
  at least one fatty substance other than fatty acids and
  at least one neutralized fatty acid,
    where the amount of fatty substance other than fatty acids in the ready to use composition is at least 10% by weight relative to the total weight of the composition and the amount of at least one neutralized fatty acid in the ready to use composition is at least 0.15% relative to the total weight of the composition.

The composition according to the invention exhibits the advantage of minimizing the drawbacks that are caused by release of ammonia.

The composition according to the invention also allows a reduction to be achieved in the discomfort likely to be sensed at the time of application of said composition to the keratin fibres, at the scalp.

Moreover, the composition allows the damage to the fibre to be reduced, relative to conventional colouring and/or bleaching compositions containing ammonia as their primary alkaline agent.

Without be bond to any theory, it is believed that the use of a neutralized fatty acid (also called soap) in specific amount allows improvement of the cationic or amphoteric polymer's deposition on hair, in relation with coacervation of polymer with soap and conductivity. Such improvement of the polymer deposition results in reducing the scalp discomfort.

When employed with oxidation bases and/or couplers and/or direct dyes, a colouring composition is obtained which has the further advantage of possessing good dyeing properties, and, more particularly, strong, colourful colorations which are relatively non-selective and which are highly resistant to the various forms of attack that the hair may undergo.

When the composition according to the invention is employed as oxidizing agent, with hydrogen peroxide for example, a bleaching or lightening composition is obtained which has the further advantage of leading to satisfactory lightening of the keratin fibres.

Other characteristics and advantages of the invention will emerge more clearly on reading the description and the examples that follow.

In the text hereinbelow, unless otherwise indicated, the limits of a range of values are included in that range. The term "at least one" associated with an ingredient of the composition means "one or more".

The human keratin fibers treated via the process according to the invention are preferably the hair.

According to a preferred embodiment, the composition contains at least one oxidation dye precursor and/or at least one direct dye, preferably at least one oxidation dye precursor.

Fatty Acid Salt

The neutralized fatty acid is under the form of a salt (or soap) and is obtained from a fatty acid and a base, the fatty acid comprising a saturated or unsaturated, linear or branched alkyl chain having at least 8 carbon atoms, preferably from 10 to 24 carbon atoms and preferably 12 to 20 carbon atoms, better still 12 to 18 carbon atoms.

For the purposes of the present invention, the term "neutralized fatty acid" according to the invention means the fatty acids that are completely neutralized by the bases (also known as saponifiers), i.e. 100% of the fatty acid is neutralized.

The degree of neutralization of the fatty acid is defined as being the weight ratio between the fatty acids in the form of salts and the total fatty acids (free fatty acids plus fatty acid salts).

According to the invention the neutralized fatty acid is completely salified and can not be considered as a fatty substance. The bases capable of being used to obtain the salts may be chosen from the alkaline agents described further below. According to one particular embodiment of the invention, the base is chosen from ammonium hydroxide, alkanolamines, and mixture thereof.

The soap is generally introduced into the composition in the form of the base on the one hand and of the fatty acid on the other hand, the formation of the salt taking place in situ.

The fatty acid salts may be chosen, in particular, from $C_{10}$ to $C_{24}$ and especially $C_{12}$-$C_{18}$ fatty acids salts and in particular salts of lauric acid, myristic acid, stearic acid, oleic acid, palmitic acid and mixtures thereof.

The soap may be more especially the salts of organic bases, such as alkanolamine like monoethanolamine, of $C_{12}$-$C_{18}$ fatty acids, more especially the salt of stearic acid and monoethanolamine.

The composition according to the invention contains at least 0.15% of neutralized fatty acid(s), preferably at least 0.2%, more preferably at least 0.4% by weight, better still at least 0.6% by weight and even better at least 0.7% relative to the total weight of the composition. According to a preferred embodiment, the composition contains at least 0.6% by weight of neutralized fatty acid(s), preferably at least 0.7% and more preferably at least 0.8% by weight relative to the total weight of the composition The amount of neutralized fatty acid(s) in the composition of the invention varies preferably from 0.15 to 15% by weight, preferably from 0.2 to 10% by weight, more preferably from 0.4 to 5% by weight and better still from 0.5 to 3% by weight relative to the total weight of the composition.

Nonionic Surfactants

The nonionic surfactants may be chosen from monooxyalkylenated or polyoxyalkylenated, monoglycerolated or polyglycerolated nonionic surfactants. The oxyalkylene units are more particularly oxyethylene or oxypropylene units, or a combination thereof, preferably oxyethylene units.

Examples of oxyalkylenated nonionic surfactants that may be mentioned include:
 oxyalkylenated ($C_8$-$C_{24}$)alkylphenols,
 saturated or unsaturated, linear or branched, oxyalkylenated $C_8$-$C_{30}$ alcohols,
 saturated or unsaturated, linear or branched, oxyalkylenated $C_8$-$C_{30}$ amides,
 esters of saturated or unsaturated, linear or branched, $C_8$-$C_{30}$ acids and of polyethylene glycols,
 polyoxyethylenated esters of saturated or unsaturated, linear or branched, $C_8$-$C_{30}$ acids and of sorbitol,
 saturated or unsaturated, oxyethylenated plant oils, such as oxyethylenated (40 or 60 EO) hydrogenated castor oil
 condensates of ethylene oxide and/or of propylene oxide, inter alia, alone or as mixtures.
 oxyalkylenated fatty acid $C_8$-$C_{30}$ esters of sorbitan, preferably oxyethylenated fatty acid $C_8$-$C_{30}$ esters of sorbitan.

The surfactants contain a number of moles of ethylene oxide and/or of propylene oxide of between 1 and 100, preferably between 2 and 80 and preferably between 2 and 50.

The oxyalkylenated nonionic surfactants are preferably chosen from oxyethylenated $C_8$-$C_{30}$ alcohols comprising from 1 to 100 mol of ethylene oxide; polyoxyethylenated esters of linear or branched, saturated or unsaturated $C_8$-$C_{30}$ acids and of sorbitol comprising from 1 to 100 mol of ethylene oxide, and saturated or unsaturated, oxyethylenated plant oils comprising from 1 to 100 mol of ethylene oxide.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

RO—[CH$_2$—CH(CH$_2$OH)—O]$_m$—H in which R represents a linear or branched $C_8$-$C_{40}$ and preferably $C_8$-$C_{30}$ alkyl or alkenyl radical, and m represents a number ranging from 1 to 30 and preferably from 1 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohols may coexist in the form of a mixture.

Among the monoglycerolated or polyglycerolated alcohols, it is more particularly preferred to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

Nonionic surfactants that may also be mentioned include non-oxyethylenated fatty acid esters of sorbitan, fatty acid esters of sucrose, optionally oxyalkylenated alkylpolyglycosides, alkylglucoside esters, derivatives of N-alkylglucamine and of N-acylmethylglucamine, aldobionamides and amine oxides.

Mention may also be made of nonionic surfactants of alkyl(poly)glycoside type, represented especially by the following general formula: $R_1O$—$(R_2O)_t$—$(G)_v$ in which:

$R_1$ represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;

$R_2$ represents an alkylene radical comprising 2 to 4 carbon atoms,

G represents a sugar unit comprising 5 to 6 carbon atoms, t denotes a value ranging from 0 to 10 and preferably 0 to 4, v denotes a value ranging from 1 to 15 and preferably 1 to 4.

Preferably, the alkylpolyglycoside surfactants are compounds of the formula described above in which:

$R_1$ denotes a linear or branched, saturated or unsaturated alkyl radical comprising from 8 to 18 carbon atoms, $R_2$ represents an alkylene radical comprising 2 to 4 carbon atoms, t denotes a value ranging from 0 to 3 and preferably equal to 0, G denotes glucose, fructose or galactose, preferably glucose;

the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an $C_8/C_{16}$ alkyl(poly)glycosides 1,4, and especially decyl glucosides and caprylyl/capryl glucosides, are most particularly preferred.

Among the commercial products, mention may be made of the products sold by the company COGNIS under the names PLANTAREN® (600 CS/U, 1200 and 2000) or PLANTACARE® (818, 1200 and 2000); the products sold by the company SEPPIC under the names ORAMIX CG 110 and ORAMIX NS 10; the products sold by the company BASF under the name LUTENSOL GD 70, or else the products sold by the company CHEM Y under the name AG10 LK.

Preferably, use is made of C8/C16-alkyl(poly)glycosides 1,4, especially as an aqueous 53% solution, such as those sold by Cognis under the reference Plantacare® 818 UP.

Among the non ionic surfactants, it is preferred, according to the invention, to use oxyalkylenated, preferably oxyethylenated, non ionic surfactants, especially chosen from saturated or unsaturated, linear or branched, oxyalkylenated, preferably chosen from oxyethylenated, $C_8$-$C_{30}$ alcohols and oxyalkylenated fatty acid $C_8$-$C_{30}$ esters of sorbitan, preferably oxyethylenated fatty acid $C_8$-$C_{30}$ esters of sorbitan. More preferably, the non ionic surfactants are chosen from oxyethylenated $C_8$-$C_{30}$ alcohols comprising from 1 to 100 mol of ethylene oxide, preferably from 1 to 50 mol of ethylene oxide, more preferably from 2 to 30 mol of ethylene oxide.

According to a specific embodiment, the composition of the invention comprises at least one oxyethylenated (OE) non-ionic surfactant comprising a number of OE units ranging from 1 to 9 and at least one oxyethylenated (OE) non-ionic surfactant comprising at least 10 OE units, said surfactants being preferably chosen from $C_8$-$C_{30}$ fatty alcohols as above described.

The total amount of non ionic surfactants preferably ranges from 0.1 to 20%, by weight, preferably from 0.5 to 15% by weight and better still from 1 to 10% by weight relative to the total weight of the composition.

Amphoteric and Cationic Non Associative Polymers

The composition according to the invention comprises one or more non associative polymer chosen from amphoteric polymers, cationic polymers and mixture thereof.

The term "amphoteric polymer" means any polymer comprising cationic groups and/or groups that can be ionized to cationic groups, and anionic groups and/or groups that can be ionized to anionic groups.

Amphoteric polymers may preferably be chosen from amphoteric polymers comprising a repetition of:
(i) one or more units derived from a monomer of (meth)acrylamide type,
(ii) one or more units derived from a monomer of (meth)acrylamidoalkyltrialkylammonium type, and
(iii) one or more units derived from an acidic monomer of (meth)acrylic acid type.

Preferably, the units derived from a monomer of (meth)acrylamide type (i) are units of structure (Ia) below:

in which $R_1$ denotes H or $CH_3$ and $R_2$ is chosen from an amino, dimethylamino, tert-butylamino, dodecylamino or —NH—$CH_2OH$ radical.

Preferably, the said amphoteric polymer comprises a repetition of only one unit of formula (Ia).

The unit derived from a monomer of (meth)acrylamide type of formula (Ia) in which $R_1$ denotes H and $R_2$ is an amino radical ($NH_2$) is particularly preferred. It corresponds to the acrylamide monomer per se.

Preferably, the units derived from a monomer of (meth)acrylamidoalkyltrialkylammonium type (ii) are units of structure (IIa) below:

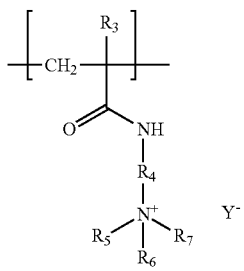

in which:
$R_3$ denotes H or $CH_3$,
$R_4$ denotes a group $(CH_2)_k$ with k being an integer ranging from 1 to 6 and preferably from 2 to 4;
$R_5$, $R_6$ and $R_7$, which may be identical or different, denote an alkyl group containing from 1 to 4 carbon atoms;
$Y^-$ is an anion such as bromide, chloride, acetate, borate, citrate, tartrate, bisulfate, bisulfite, sulfate or phosphate.

Preferably, the said amphoteric polymer comprises a repetition of only one unit of formula (IIa).

Among these units derived from a monomer of (meth)acrylamidoalkyltrialkylammonium type of formula (IIa), the ones that are preferred are those derived from the methacrylamidopropyltrimethylammonium chloride monomer, for which $R_3$ denotes a methyl radical, k is equal to 3, $R_5$, $R_6$ and $R_7$ denote a methyl radical, and Y-denotes a chloride anion.

Preferably, the units derived from a monomer of (meth)acrylic acid type (iii) are units of formula (IIIa):

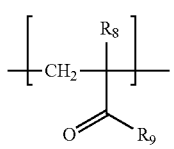

in which $R_8$ denotes H or $CH_3$ and $R_9$ denotes a hydroxyl radical or a —NH—$C(CH_3)_2$—$CH_2$—$SO_3H$ radical.

The preferred units of formula (IIIa) correspond to the acrylic acid, methacrylic acid and 2-acrylamino-2-methylpropanesulfonic acid monomers.

Preferably, the unit derived from a monomer of (meth)acrylic acid type of formula (IIIa) is that derived from acrylic acid, for which $R_8$ denotes a hydrogen atom and $R_9$ denotes a hydroxyl radical.

The acidic monomer(s) of (meth)acrylic acid type may be non-neutralized or partially or totally neutralized with an organic or mineral base.

Preferably, the said amphoteric polymer comprises a repetition of only one unit of formula (IIa).

According to a preferred embodiment of the invention, the amphoteric polymer(s) of this type comprise at least 30 mol % of units derived from a monomer of (meth)acrylamide type (i). Preferably, they comprise from 30 mol % to 70 mol % and more preferably from 40 mol % to 60 mol % of units derived from a monomer of (meth)acrylamide type.

The content of units derived from a monomer of (meth)acrylamidoalkyltrialkylammonium type (ii) may advantageously be from 10 mol % to 60 mol % and preferentially from 20 mol % to 55 mol %.

The content of units derived from an acidic monomer of (meth)acrylic acid type (iii) may advantageously be from 1 mol % to 20 mol % and preferentially from 5 mol % to 15 mol %.

According to a particularly preferred embodiment of the invention, the amphoteric polymer of this type comprises:
from 30 mol % to 70 mol % and more preferably from 40 mol % to 60 mol % of units derived from a monomer of (meth)acrylamide type (i),
from 10 mol % to 60 mol % and preferentially from 20 mol % to 55 mol % of units derived from a monomer of (meth)acrylamidoalkyltrialkylammonium type (ii), and
from 1 mol % to 20 mol % and preferentially from 5 mol % to 15 mol % of units derived from a monomer of (meth)acrylic acid type (iii).

Amphoteric polymers of this type may also comprise additional units, other than the units derived from a monomer of (meth)acrylamide type, of (meth)acrylamidoalkyltrialkylammonium type and of (meth)acrylic acid type as described above.

However, according to a preferred embodiment of the invention, the said amphoteric polymers consist solely of units derived from monomers (i) of (meth)acrylamide type, (ii) of (meth)acrylamidoalkyltrialkylammonium type and (iii) of (meth)acrylic acid type.

As examples of amphoteric polymers that are particularly preferred, mention may be made of acrylamide/methacrylamidopropyltrimethylammonium chloride/acrylic acid terpolymers. Such polymers are listed in the CTFA Dictionary (International Cosmetic Ingredient Dictionary) under the name Polyquaternium 53. Corresponding products are especially sold under the names Merquat 2003 and Merquat 2003 PR by the company Nalco.

As another type of preferred amphoteric polymer that may be used, mention may also be made of copolymers based on (meth)acrylic acid and on a dialkyldiallylammonium salt, such as copolymers of (meth)acrylic acid and of dimethyldiallylammonium chloride. An example that may be mentioned is Merquat 280 sold by the company Nalco.

The term "cationic polymer" means any polymer comprising cationic groups and/or groups that can be ionized to cationic groups, without anionic groups and/or groups that can be ionized to anionic groups. The preferred cationic polymers are chosen from those that contain units comprising primary, secondary, tertiary and/or quaternary amine groups that may either form part of the main polymer chain or may be borne by a side substituent directly connected thereto.

The cationic polymers that may be used preferably have a weight-average molar mass (Mw) of between 500 and $5 \times 10^6$ approximately and preferably between $10^3$ and $3 \times 10^6$ approximately.

Among the cationic polymers, mention may be made more particularly of:

(1) homopolymers or copolymers derived from acrylic or methacrylic esters or amides and comprising at least one of the units of the following formulae:

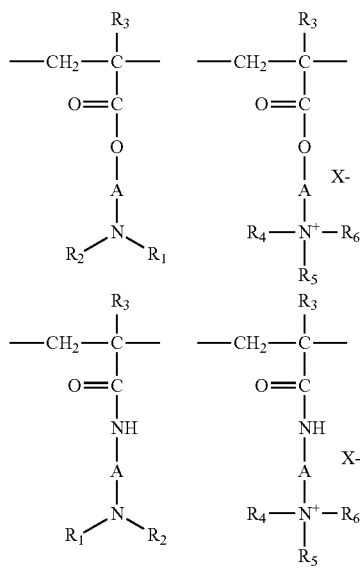

in which:

R3, which may be identical or different, denote a hydrogen atom or a $CH_3$ radical;

A, which may be identical or different, represent a linear or branched divalent alkyl group of 1 to 6 carbon atoms, preferably 2 or 3 carbon atoms, or a hydroxyalkyl group of 1 to 4 carbon atoms;

R4, R5 and R6, which may be identical or different, represent an alkyl group containing from 1 to 18 carbon atoms or a benzyl radical, preferably an alkyl group containing from 1 to 6 carbon atoms;

R1 and R2, which may be identical or different, represent a hydrogen atom or an alkyl group containing from 1 to 6 carbon atoms, preferably methyl or ethyl;

X denotes an anion derived from a mineral or organic acid, such as a methosulfate anion or a halide such as chloride or bromide.

The copolymers of family (1) may also contain one or more units derived from comonomers that may be selected from the family of acrylamides, methacrylamides, diacetone acrylamides, acrylamides and methacrylamides substituted on the nitrogen with lower ($C_1$-$C_4$) alkyls, acrylic or methacrylic esters thereof, vinyllactams such as vinylpyrrolidone or vinylcaprolactam, and vinyl esters.

(2) Cationic polysaccharides, especially cationic celluloses and galactomannan gums.

Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

(3) Polymers formed from piperazinyl units and divalent alkylene or hydroxyalkylene radicals containing straight or branched chains, optionally interrupted with oxygen, sulfur or nitrogen atoms or with aromatic or heterocyclic rings, and also the oxidation and/or quaternization products of these polymers.

(4) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they comprise one or more tertiary amine functions, they can be quaternized.

(5) Polyamino amide derivatives resulting from the condensation of polyalkylene polyamines with polycarboxylic acids followed by alkylation with bifunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl.

(6) Polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid preferably being between 0.8:1 and 1.4:1; the resulting polyamino amide being reacted with epichlorohydrin in a mole ratio of epichlorohydrin relative to the secondary amine group of the polyamino amide preferably of between 0.5:1 and 1.8:1.

(7) Cyclopolymers of alkyldiallylamine or of dialkyldiallylammonium, such as the homopolymers or copolymers containing, as main constituent of the chain, units corresponding to formula (I) or (II):

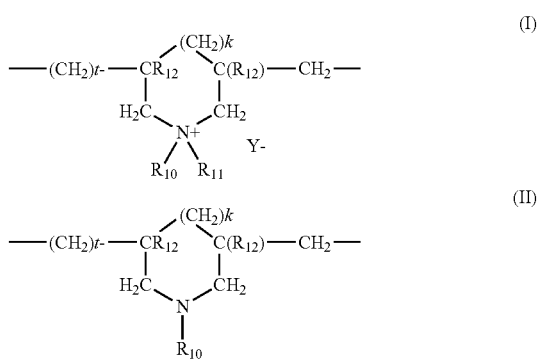

in which:

k and t are equal to 0 or 1, the sum k+t being equal to 1;

R12 denotes a hydrogen atom or a methyl radical;

R10 and R11, independently of each other, denote a $C_1$-$C_6$ alkyl group, a hydroxyl($C_1$-$C_5$)alkyl group, a $C_1$-$C_4$ amidoalkyl group; or alternatively R10 and R11 may denote, together with the nitrogen atom to which they are attached, an heterocyclic group such as piperidinyl or morpholinyl; R10 and R11, independently of each other, preferably denote a $C_1$-$C_4$ alkyl group;

$Y^-$ is an anion such as bromide, chloride, acetate, borate, citrate, tartrate, bisulfate, bisulfite, sulfate or phosphate.

Mention may be made more particularly of the dimethyldiallylammonium salt (for example chloride) homopolymer sold for example under the name MERQUAT 100 by the company Nalco, and the copolymers of diallyldimethylammonium salts (for example chloride) and of acrylamide, sold especially under the name MERQUAT 550 or MERQUAT 7SPR.

(8) Quaternary diammonium polymers comprising repeating units of formula:

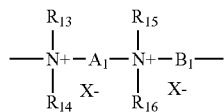

(III)

in which:

R13, R14, R15 and R16, which may be identical or different, represent aliphatic, alicyclic or arylaliphatic radicals comprising from 1 to 20 carbon atoms, or $C_1$-$C_{12}$ hydroxyalkylaliphatic radicals, or else R13, R14, R15 and R16, together or separately, constitute, with the nitrogen atoms to which they are attached, heterocycles optionally comprising a second non-nitrogen heteroatom, or else R13, R14, R15 and R16 represent a linear or branched $C_1$-$C_6$ alkyl radical substituted with a nitrile, ester, acyl, amide or —CO—O—R17-D or —CO—NH—R17-D group in which R17 is an alkylene and D is a quaternary ammonium group;

A1 and B1 represent divalent polymethylene groups comprising from 2 to 20 carbon atoms, linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^+$ denotes an anion derived from a mineral or organic acid;

it being understood that A1, R13 and R15 can form, with the two nitrogen atoms to which they are attached, a piperazine ring;

in addition, if A1 denotes a linear or branched, saturated or unsaturated alkylene or hydroxyalkylene radical, B1 may also denote a group $(CH_2)_n$—CO-D-OC—$(CH_2)_p$—wherein n and p, which may be identical or different, denote an integer from 2 to 20, and wherein D denotes:

a) a glycol residue of formula —O—Z—O—, in which Z denotes a linear or branched hydrocarbon-based radical, or a group corresponding to one of the following formulae: —$(CH_2$—$CH_2$—$O)_x$—$CH_2$—$CH_2$— and —[$CH_2$—CH($CH_3$)—O]$_y$—$CH_2$—CH($CH_3$)—, where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or else the divalent radical —$CH_2$—$CH_2$—S—S—$CH_2$—$CH_2$—;

d) a ureylene group of formula: —NH—CO—NH—;

Preferably, $X^+$ is an anion such as chloride or bromide. These polymers have a number-average molar mass (Mn) generally of between 1000 and 100 000.

Mention may be made more particularly of polymers that are composed of repeating units corresponding to the formula:

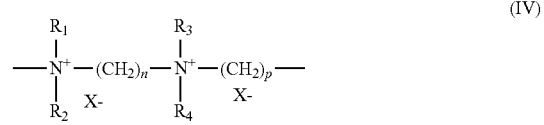

(IV)

in which R1, R2, R3 and R4, which may be identical or different, denote an alkyl or hydroxyalkyl radical containing from 1 to 4 carbon atoms, n and p are integers ranging from 2 to 20, and $X^-$ is an anion derived from an organic or mineral acid.

A particularly preferred compound of formula (IV) is that for which R1, R2, R3 and R4 represent a methyl radical and n=3, p=6 and X=Cl, known as Hexadimethrine chloride according to the INCI (CTFA) nomenclature.

(9) Polyquaternary ammonium polymers comprising units of formula (V):

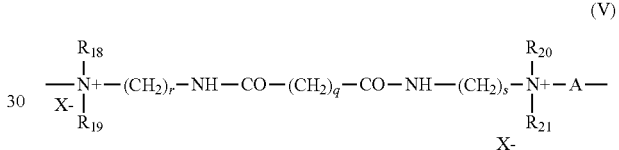

(V)

in which:

R18, R19, R20 and R21, which may be identical or different, represent a hydrogen atom or a methyl, ethyl, propyl, β-hydroxyethyl, β-hydroxypropyl or —$CH_2CH_2$($OCH_2CH_2$)$_p$OH group, in which p is equal to 0 or to an integer between 1 and 6, with the proviso that R18, R19, R20 and R21 do not simultaneously represent a hydrogen atom, r and s, which may be identical or different, are integers between 1 and 6, q is equal to 0 or to an integer between 1 and 34, $X^-$ denotes an anion such as a halide, A denotes a dihalide radical or preferably represents —$CH_2$—$CH_2$—O—$CH_2$—$CH_2$—.

(10) Quaternary polymers of vinylpyrrolidone and of vinylimidazole, for instance the products sold under the names Luviquat® FC 905, FC 550 and FC 370 by the company BASF.

(11) Polyamines such as Polyquart® H sold by Cognis, referred to under the name Polyethylene glycol (15) tallow polyamine in the CTFA dictionary.

(12) Polymers comprising in their structure:

(a) one or more units corresponding to formula (A) below:

(A)

(b) optionally, one or more units corresponding to formula (B) below:

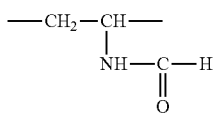

(B)

In other words, these polymers may be chosen especially from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to formula (A) and from 0 to 95 mol % of units corresponding to formula (B), preferentially from 10 mol % to 100 mol % of units corresponding to formula (A) and from 0 to 90 mol % of units corresponding to formula (B).

The weight-average molecular mass of the said polymer, measured by light scattering, may range from 1000 to 3 000 000 g/mol, preferably from 10 000 to 1 000 000 g/mol and more particularly from 100 000 to 500 000 g/mol.

Other cationic polymers that may be used in the context of the invention are cationic proteins or cationic protein hydrolysates, polyalkyleneimines, in particular polyethyleneimines, polymers comprising vinylpyridine or vinylpyridinium units, condensates of polyamines and of epichlorohydrin, quaternary polyureylenes and chitin derivatives.

Preferably, the cationic polymers are chosen from the polymers of families (1), (2), (7) (8) and (10) mentioned above, preferably families (7) and (8).

Among the cationic polymers mentioned above, the ones that may preferably be used are cationic cyclopolymers, in particular dimethyldiallylammonium salt (for example chloride) homopolymers or copolymers, sold under the names Merquat 100, Merquat 550 and Merquat S by the company Nalco, hexadimethrine chloride and mixtures thereof.

The composition according to the invention may comprise the cationic and/or amphoteric polymers in an amount of between 0.01% and 5% by weight, especially from 0.05% to 3% by weight and preferentially from 0.1% to 2% by weight, relative to the composition.

According to a specific embodiment, the at least neutralized fatty acid and at least cationic and/or amphoteric polymers are present in a ratio neutralized fatty acid/cationic and/or amphoteric polymers ranging from 0.2 to 4, preferably from 0.3 to 3.5 and most preferably from 0.4 to 3.

Fatty Substances

As previously indicated, the composition according to the invention comprises one or more fatty substances other than fatty acids, the total amount of fatty substances representing at least 10% by weight, preferably at least 12% by weight, relative to the weight of the composition.

The term "fatty substance" is intended to mean an organic compound that is insoluble in water at ordinary temperature (25° C.) and at atmospheric pressure (760 mmHg) (solubility of less than 5%, preferably less than 1% and even more preferentially less than 0.1%). They bear in their structure at least one hydrocarbon-based chain comprising at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

The term "oil" is intended to mean a "fatty substance" that is liquid at ambient temperature (25° C.) and at atmospheric pressure (760 mmHg or $1.013 \times 10^5$ Pa).

The term "non-silicone oil" is intended to mean an oil not containing any silicon atoms (Si) and the term "silicone oil" is intended to mean an oil containing at least one silicon atom.

More particularly, the fatty substances are chosen from $C_6$-$C_{16}$ hydrocarbons, hydrocarbons containing more than 16 carbon atoms, non-silicone oils of animal origin, triglycerides of plant or synthetic origin, fluoro oils, fatty alcohols, esters of fatty acids and/or of fatty alcohols other than triglycerides, non-silicone waxes other than solid fatty alcohols and than solid synthetic esters, and silicones, and mixtures thereof.

It is recalled that, for the purposes of the invention, fatty alcohols, esters and acids more particularly have at least one linear or branched, saturated or unsaturated hydrocarbon-based group comprising 8 to 30 carbon atoms, which is optionally substituted, in particular with one or more hydroxyl groups (in particular 1 to 4). If they are unsaturated, these compounds may comprise one to three conjugated or unconjugated carbon-carbon double bonds.

The linear or branched hydrocarbons of inorganic or synthetic origin containing more than 16 carbon atoms are preferably chosen from liquid paraffins or liquid petroleum jelly, petroleum jelly, polydecenes and hydrogenated polyisobutene such as Parleam®, and mixtures thereof.

As regards the $C_6$-$C_{16}$ lower alkanes, they are linear or branched, or possibly cyclic.

Examples that may be mentioned include hexane, cyclohexane, undecane, dodecane, tridecane or isoparaffins, such as isohexadecane, isodecane or isododecane, and mixtures thereof.

A hydrocarbon-based oil of animal origin that may be mentioned is perhydrosqualene.

The triglycerides of plant or synthetic origin are preferably chosen from liquid fatty acid triglycerides comprising from 8 to 30 carbon atoms, for instance heptanoic or octanoic acid triglycerides, or alternatively, more particularly from those present in plant oils, for instance sunflower oil, corn oil, soybean oil, marrow oil, grapeseed oil, sesame seed oil, hazelnut oil, apricot oil, macadamia oil, arara oil, castor oil, avocado oil, jojoba oil, shea butter oil or synthetic caprylic/capric acid triglycerides, for instance those sold by the company Stearineries Dubois or those sold under the names Miglyol® 810, 812 and 818 by the company Dynamit Nobel, and mixtures thereof.

The fluoro oils may be chosen from perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the invention are more particularly chosen from linear or branched, saturated or unsaturated alcohols containing from 8 to 30 carbon atoms. Examples that may be mentioned include cetyl alcohol, stearyl alcohol and a mixture thereof (cetylstearyl alcohol), octyldodecanol, 2-butyloctanol, 2-hexyldecanol, 2-undecylpentadecanol, oleyl alcohol, linolenyl alcohol, ricinoleyl alcohol, undecylenyl alcohol and linoleyl alcohol, and mixtures thereof.

As regards the esters of fatty acids and/or of fatty alcohols other than the triglycerides mentioned above and plant waxes, mention may be made in particular of esters of saturated or unsaturated, linear $C_1$-$C_{26}$ or branched $C_3$-$C_{26}$ aliphatic monoacids or polyacids and of saturated or unsaturated, linear $C_1$-$C_{26}$ or branched $C_3$-$C_{26}$ aliphatic monoalcohols or polyalcohols, the total carbon number of the esters being greater than or equal to 6 and more advantageously greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate, and mixtures thereof, and mixtures thereof.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

Mention may be made in particular of: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates, and mixtures thereof.

Among the esters mentioned above, it is preferred to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate, and mixtures thereof.

The composition may also comprise, as fatty ester, sugar esters and diesters of $C_6$-$C_{30}$ and preferably $C_{12}$-$C_{22}$ fatty acids. It is recalled that the term "sugar" is intended to mean oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, in particular alkyl derivatives, such as methyl derivatives, for instance methylglucose.

The sugar esters of fatty acids may be chosen in particular from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or unconjugated carbon-carbon double bonds.

The esters according to this variant may also be chosen from monoesters, diesters, triesters, tetraesters and polyesters, and mixtures thereof.

These esters may be, for example, oleates, laurates, palmitates, myristates, behenates, cocoates, stearates, linoleates, linolenates, caprates or arachidonates, or mixtures thereof such as, in particular, oleate/palmitate, oleate/stearate or palmitate/stearate mixed esters.

More particularly, use is made of monoesters and diesters and in particular mono- or di-oleate, -stearate, -behenate, -oleate/palmitate, -linoleate, -linolenate or -oleate/stearate of sucrose, glucose or methylglucose.

An example that may be mentioned is the product sold under the name Glucate® DO by the company Amerchol, which is a methylglucose dioleate.

Examples of esters or mixtures of esters of sugar of fatty acid that may also be mentioned include:
the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name Ryoto Sugar Esters, for example referenced B370 and corresponding to sucrose behenate formed from 20% monoester and 80% diester, triester and polyester;
the sucrose monodipalmitostearate sold by the company Goldschmidt under the name Tegosoft® PSE.

The non-silicone wax(es) other than solid fatty alcohols and solid synthetic esters are chosen in particular from carnauba wax, candelilla wax, esparto wax, paraffin wax, ozokerite, plant waxes, such as olive tree wax, rice wax, hydrogenated jojoba wax or absolute flower waxes, such as the blackcurrant blossom essential wax sold by the company Bertin (France), or animal waxes, such as beeswaxes or modified beeswaxes (cerabellina); other waxes or waxy raw materials that may be used according to the invention are in particular marine waxes, such as the product sold by the company Sophim under the reference M82, polyethylene waxes or polyolefin waxes in general.

The silicones that may be used in the cosmetic compositions of the present invention are volatile or non-volatile, cyclic, linear or branched silicones, which are unmodified or modified with organic groups, having a viscosity of $5\times10^{-6}$ to 2.5 m$^2$/s at 25° C., and preferably $1\times10^{-5}$ to 1 m$^2$/s.

The silicones that may be used in accordance with the invention may be in the form of oils or waxes.

Preferably, the silicone is chosen from polydialkylsiloxanes, in particular polydimethylsiloxanes (PDMSs), and organomodified polysiloxanes comprising at least one functional group chosen from poly(oxyalkylene) groups, amino groups and alkoxy groups.

Organopolysiloxanes are defined in greater detail in Walter Noll's Chemistry and Technology of Silicones (1968), Academic Press. They may be volatile or non-volatile.

When they are volatile, the silicones are more particularly chosen from those with a boiling point of between 60° C. and 260° C., and even more particularly from:

(i) cyclic polydialkylsiloxanes comprising from 3 to 7 and preferably 4 to 5 silicon atoms. These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, and Silbione® 70045 V5 by Rhodia, and mixtures thereof.

Mention may also be made of cyclocopolymers of the dimethylsiloxane/methylalkylsiloxane type, such as Volatile Silicone® FZ 3109 sold by the company Union Carbide, of formula:

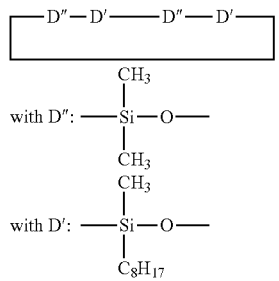

Mention may also be made of mixtures of cyclic polydialkylsiloxanes with organosilicon compounds, such as the mixture of octamethylcyclotetrasiloxane and tetra(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, P. 27-32—Todd & Byers "Volatile Silicone fluids for cosmetics".

Use is preferably made of non-volatile polydialkylsiloxanes, polydialkylsiloxane gums and resins, polyorganosiloxanes modified by the organofunctional groups above, and mixtures thereof.

These silicones are more particularly chosen from polydialkylsiloxanes, among which mention may be made mainly of polydimethylsiloxanes bearing trimethylsilyl end groups. The viscosity of the silicones is measured at 25° C. according to Standard ASTM 445 Appendix C.

Among these polydialkylsiloxanes, mention may be made, in a nonlimiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes bearing dimethylsilanol end groups known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

The fatty substance(s) does (do) not comprise any $C_2$-$C_3$ oxyalkylene units. Preferably, they do not contain any glycerolated units.

According to one preferred variant, the fatty substances are not silicone-based.

The fatty substances are preferably chosen from $C_6$-$C_{16}$ hydrocarbons, hydrocarbons comprising more than 16 carbon atoms, non-silicone oils of animal origin, triglycerides of plant or synthetic origin, fatty alcohols, fatty acid and/or fatty alcohol esters, or mixtures thereof.

According to an embodiment, the composition of the invention comprises:

at least one fatty substance that is liquid at ambient temperature and at atmospheric pressure, preferably chosen from $C_6$-$C_{16}$ hydrocarbons, hydrocarbons comprising more than 16 carbon atoms, non-silicone oils of animal origin, triglycerides of plant or synthetic origin and mixture thereof and at least one fatty alcohol which is solid at room temperature and at atmospheric pressure, preferably chosen from cetyl alcohol (1-hexadecanol), stearyl alcohol (1-octadecanol) and mixture thereof such as cetylstearyl alcohol.

The composition according to the invention comprises at least 10%, preferably at least 12% by weight of fatty substances other than fatty acids, relative to the total weight of the composition. The composition according to the invention more particularly has a fatty substance other than fatty acids content ranging from 10% to 40% by weight, even better still from 12% to 20% by weight, relative to the weight of the composition.

Associative Polymers

According to an embodiment, the composition of the invention may contain at least an associative polymer.

For the purposes of the present invention, the term "associative polymers" means water-soluble polymers that are capable, in an aqueous medium, of reversibly combining with each other or with other molecules.

Their chemical structure comprises at least one hydrophilic region and at least one hydrophobic region characterized by at least one $C_8$-$C_{30}$ fatty chain.

The associative polymers according to the invention may be of anionic, cationic, amphoteric or nonionic type.

Associative polymers of nonionic type

According to the invention, they are preferentially chosen from:

(1) celluloses modified with groups comprising at least one fatty chain; examples that may be mentioned include:

hydroxyethylcelluloses modified with groups comprising at least one fatty chain, such as linear or branched alkyl, linear or branched arylalkyl or linear or branched alkylaryl groups, or mixtures thereof, and in which the linear or branched alkyl groups are preferably $C_8$-$C_{22}$, for instance the product Natrosol Plus Grade 330 CS® ($C_{16}$ alkyl) sold by the company Aqualon, the product Polysurf 67 CS (cetylhydroxyethylcellulose) sold by the company Ashland or the product Bermocoll EHM 100® sold by the company Berol Nobel, hydroxyethylcelluloses modified with alkylphenyl polyalkylene glycol ether groups, such as the product Amercell Polymer HM-1500® (polyethylene glycol (15) nonylphenyl ether) sold by the company Amerchol, hydroxypropylmethylcelluloses modified with linear or branched $C_8$-$C_{22}$ alkyl groups, for instance the product Sangelose 60L (INCI name: hydroxypropyl methylcellulose stearoxy ether) sold by the company Daido Chemical, (2) hydroxypropyl guars modified with groups comprising at least one fatty chain, such as the product Esaflor HM 22® ($C_{22}$ alkyl chain) sold by the company Lamberti, and the products RE210-18® ($C_{14}$ alkyl chain) and RE205-1® ($C_{20}$ alkyl chain) sold by the company Rhone-Poulenc, (3) copolymers of vinylpyrrolidone and of fatty-chain hydrophobic monomers; examples that may be mentioned include:

the products Antaron V216® and Ganex V216® (vinylpyrrolidone/hexadecene copolymer) sold by the company ISP.

the products Antaron V220® and Ganex V220® (vinylpyrrolidone/eicosene copolymer) sold by the company ISP, (4) copolymers of $C_1$-$C_6$ alkyl methacrylates or acrylates and of amphiphilic monomers comprising at least one fatty chain, for instance the oxyethylenated methyl acrylate/stearyl acrylate copolymer sold by the company Goldschmidt under the name Antil 208®, (5) copolymers of hydrophilic methacrylates or acrylates and of hydrophobic monomers comprising at least one fatty chain, for instance the polyethylene glycol methacrylate/lauryl methacrylate copolymer, (6) polyurethane polyethers comprising in their chain both hydrophilic blocks usually of polyoxyethylenated nature and hydrophobic blocks, which may be aliphatic sequences alone and/or cycloaliphatic and/or aromatic sequences, (7) polymers with an aminoplast ether backbone containing at least one fatty chain, such as the Pure Thix® compounds sold by the company Sud-Chemie.

Preferably, the polyurethane polyethers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be included. In addition, the polymer may comprise a hydrocarbon-based chain at one end or at both ends of a hydrophilic block.

The polyurethane polyethers may be multiblock, in particular in triblock form. The hydrophobic blocks may be at each end of the chain (for example: triblock copolymer containing a hydrophilic central block) or distributed both at the ends and in the chain (for example multiblock copolymer). These same polymers may also be graft polymers or star polymers.

The nonionic fatty-chain polyurethane polyethers may be triblock copolymers in which the hydrophilic block is a polyoxyethylenated chain comprising from 50 to 1000 oxyethylene groups. The nonionic polyurethane polyethers comprise a urethane bond between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used in the invention, it is also possible to use Rheolate 205® containing a urea function, sold by the company Rheox, or Rheolate® 208, 204 or 212, and also Acrysol RM 184®.

Mention may also be made of the product Elfacos T210® containing a $C_{12-14}$ alkyl chain, and the product Elfacos T212® containing a Ca8 alkyl chain, from Akzo.

The product DW 1206B® from Rohm & Haas containing a $C_{20}$ alkyl chain and a urethane bond, sold at a solids content of 20% in water, may also be used.

It is also possible to use solutions or dispersions of these polymers, especially in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Rohm & Haas may also be used.

Mention may also be made of Luvigel Star (polyurethane-39) sold by the company BASF, which is a copolymer of PEG-140 and of hexamethylene diisocyanate terminated with $C_{12-14}$ pareth-10, $C_{16-18}$ pareth-11 and $C_{18-20}$ pareth-11.

The polyurethane polyethers that may be used according to the invention are in particular those described in the article by G. Fonnum, J. Bakke and Fk. Hansen—Colloid Polym. Sci. 271, 380-389 (1993).

Even more particularly, according to the invention, it is preferred to use a polyurethane polyether that may be obtained by polycondensation of at least three compounds comprising:

(i) at least one polyethylene glycol comprising from 150 to 180 mol of ethylene oxide, (ii) stearyl alcohol or decyl alcohol and (iii) at least one diisocyanate.

Such polyurethane polyethers are sold especially by the company Rohm & Haas under the names Aculyn 46® and Aculyn 44® [Aculyn 46® is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44® is a polycondensate of polyethylene glycol containing 150 or 180 mol of ethylene oxide, of decyl alcohol and of methylenebis(4-cyclohexyl isocyanate) (SMDI), at 35% by weight in a mixture of propylene glycol (39%) and water (26%)].

In one preferred embodiment according to the present invention, the associative polymers are chosen from non ionic associative polymers, as described above and more specifically from non ionic cellulose derivatives.

The associative polymer(s) may be present in an amount ranging from 0.005% to 5% by weight, preferably in an amount ranging from 0.01% to 2% by weight relative to the total weight of the composition.

Alkaline Agent

The ready to use composition comprises one or more alkaline agent(s). This agent may be chosen from mineral or organic or hybrid alkaline agents, or mixtures thereof.

The mineral alkaline agent(s) are preferably chosen from aqueous ammonia, alkali metal carbonates or bicarbonates such as sodium or potassium carbonates and sodium or potassium bicarbonates, sodium hydroxide or potassium hydroxide, or mixtures thereof.

The organic alkaline agent(s) are preferably chosen from organic amines with a pKb at 25° C. of less than 12, preferably less than 10 and even more advantageously less than 6. It should be noted that it is the pKb corresponding to the function of highest basicity.

Hybrid compounds that may be mentioned include the salts of the amines mentioned previously with acids such as carbonic acid or hydrochloric acid.

The organic alkaline agent(s) are chosen, for example, from alkanolamines, oxyethylenated and/or oxypropylenated ethylenediamines, amino acids and the compounds of formula (VI) below:

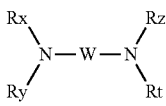
(VI)

in which W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and one or more linear or branched $C_1$-$C_8$ alkyl groups bearing one or more hydroxyl radicals.

Alkanolamines such as monoalkanolamines, dialkanolamines or trialkanolamines comprising from one to three identical or different $C_1$-$C_4$ hydroxyalkyl radicals are in particular suitable for performing the invention.

Among compounds of this type, mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function chosen more particularly from carboxylic acid, sulfonic acid, phosphonic acid or phosphoric acid functions. The amino acids may be in neutral or ionic form.

As amino acids that may be used in the present invention, mention may be made especially of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (VII) below:

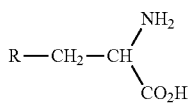
(VII)

in which R denotes a group chosen from:

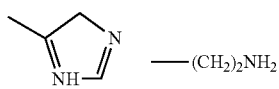

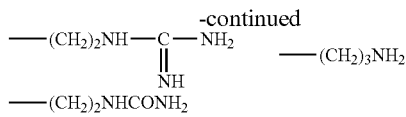

The compounds corresponding to formula (VII) are histidine, lysine, arginine, ornithine and citrulline.

The organic amine may also be chosen from organic amines of heterocyclic type. Besides histidine that has already been mentioned in the amino acids, mention may be made in particular of pyridine, piperidine, imidazole, triazole, tetrazole and benzimidazole.

The organic amine may also be chosen from amino acid dipeptides. As amino acid dipeptides that may be used in the present invention, mention may be made especially of carnosine, anserine and baleine.

The organic amine is chosen from compounds comprising a guanidine function. As amines of this type that may be used in the present invention, besides arginine, which has already been mentioned as an amino acid, mention may be made especially of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

Mention may be made in particular of the use of guanidine carbonate or monoethanolamine hydrochloride as hybrid compounds.

The composition of the invention preferably contains one or more alkanolamines, preferably monoethanolamine and/or aqueous ammonia as alkaline agents.

Advantageously, the composition according to the invention has a content of alkaline agent(s) ranging from 0.01% to 30% by weight, preferably from 0.1% to 20% by weight and better still from 1% to 10% by weight relative to the weight of said composition.

Dyes

According to a preferred embodiment, the composition contains at least one oxidation dye precursor and/or at least one direct dye, preferably at least one oxidation dye precursor.

Oxidation bases and couplers may be used as oxidation dye precursors.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(3-hydroxyethyl)-para-phenylenediamine, 4-N,N-bis(p-hydroxyethyl)amino-2-methylaniline, 4-N,N-bis(β-hydroxyethyl)amino-2-chloroaniline, 2-p-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-p-hydroxyethyl)-para-phenylenediamine, N-(β,γ-dihydroxypropyl)-para-phenylenediamine, N-(4'-aminophenyl)-paraphenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(3-hydroxyethyl)-N,N'-bis(4'-aminophenyl)ethylenediamine, N,N'-bis(4-aminophenyl)tetramethylenediamine, N,N'-bis(3-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-ylpyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in the patents DE 2359399; JP 88-169571; JP 05-63124; EP 0770375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Among the pyrazole derivatives that may be mentioned are the compounds described in the patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(p-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethyl-pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts. 4,5-diamino-1-(β-methoxyethyl)pyrazole may also be used.

A 4,5-diaminopyrazole will preferably be used, and even more preferentially 4,5-diamino-1-(3-hydroxyethyl)pyrazole and/or a salt thereof.

Pyrazole derivatives that may also be mentioned include diamino-N,N-dihydro-pyrazolopyrazolones and especially those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one, 2,3-diamino-6-hydroxy-6,7-dihydro-1H,5H-pyrazolo[1,2-a]pyrazol-1-one. 2,3-Diamino-6,7-dihydro-1H,5H-pyrazolo[1,2-a]pyrazol-1-one and/or a salt thereof will preferably be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof will preferentially be used as heterocyclic bases.

Among the couplers that may be used in the composition of the invention, mention may be made especially of meta-phenylenediamines, meta-aminophenols, meta-diphenols, naphthalene-based couplers and heterocyclic couplers, and also the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxyethyloxy)-benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylamino-benzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxy-ethylamino)toluene, 6-hydroxyindoline, 2,6-dihydroxy-4-methylpyridine, 1-H-3-methyl-pyrazol-5-one, 1-phenyl-3-methylpyrazol-5-one, 2,6-dimethylpyrazolo-[1,5-b]-1,2,4-triazole, 2,6-dimethyl-[3,2-c]-1,2,4-triazole and 6-methylpyrazolo[1,5-a]-benzimidazole, the addition salts thereof with an acid, and mixtures thereof.

The addition salts of the oxidation bases and couplers are especially chosen from the addition salts with an acid such as the hydrochlorides, hydrobromides, sulfates, citrates, succinates, tartrates, lactates, tosylates, benzenesulfonates, phosphates and acetates.

The oxidation base(s) are each generally present in an amount of from 0.0001% to 10% by weight relative to the total weight of the composition, and preferably from 0.005% to 5% by weight relative to the total weight of the composition.

The coupler(s) each generally represent from 0.0001% to 10% by weight relative to the total weight of the composition, and preferably from 0.005% to 5% by weight relative to the total weight of the composition.

The composition according to the invention may contain cationic or nonionic synthetic or natural direct dyes.

Examples of particularly suitable direct dyes that may be mentioned include nitrobenzene dyes; azo direct dyes; azomethine direct dyes; methine direct dyes; azacarbocyanin direct dyes, for instance tetraazacarbocyanins (tetraaza-pentamethines); quinone and in particular anthraquinone, naphthoquinone or benzoquinone direct dyes; azine direct dyes; xanthene direct dyes; triarylmethane direct dyes; indoamine direct dyes; indigoid direct dyes; phthalocyanine direct dyes, porphyrin direct dyes and natural direct dyes, alone or as mixtures. In particular, mention may be made of direct dyes from among: azo; methine; carbonyl; azine; nitro (hetero)aryl; tri(hetero)arylmethane; porphyrin; phthalocyanine and natural direct dyes, alone or as mixtures.

When they are present, the direct dye(s) more particularly represent from 0.0001% to 10% by weight and preferably from 0.005% to 5% by weight of the total weight of the composition.

Oxidizing Agent(s)

The composition according to the invention also comprises one or more oxidizing agent(s).

The oxidizing agents are chosen, for example, from hydrogen peroxide, urea peroxide, alkali metal bromates or ferricyanides, peroxygenated salts, for instance persulfates, perborates, peracids and precursors thereof and percarbonates of alkali metals or alkaline-earth metals. Advantageously, the oxidizing agent is hydrogen peroxide.

The content of oxidizing agent(s) more particularly represents from 0.1% to 40% by weight, preferably from 0.5% to 20% by weight and more preferably 1% to 15% relative to the weight of the composition.

The composition of the invention may also contain various adjuvants conventionally used in compositions for dyeing or lightening the hair, such as cationic surfactants, anionic or nonionic non associative polymers or mixtures thereof; antioxidants; penetrants; sequestrants; fragrances; dispersants; film-forming agents; ceramides; preserving agents; opacifiers.

The above adjuvants are generally present in an amount for each of them of between 0.01% and 20% by weight relative to the weight of the composition.

The composition according to the invention may comprise water and/or one or more organic solvents.

Examples of organic solvents that may be mentioned include linear or branched and preferably saturated monoalcohols or diols, comprising 2 to 10 carbon atoms, such as ethanol, isopropanol, hexylene glycol (2-methyl-2,4-pentanediol), neopentyl glycol and 3-methyl-1,5-pentanediol, butylene glycol, dipropylene glycol and propylene glycol; aromatic alcohols such as benzyl alcohol or phenylethyl alcohol; polyols containing more than two hydroxyl functions, such as glycerol; polyol ethers, for instance ethylene glycol monomethyl, monoethyl or monobutyl ether, propylene glycol or ethers thereof, for instance propylene glycol monomethyl ether; and also diethylene glycol alkyl ethers, especially $C_1$-$C_4$ alkyl ethers, for instance diethylene glycol monoethyl ether or monobutyl ether, alone or as a mixture.

The organic solvents, when they are present, generally represent between 0.1% and 40% by weight relative to the total weight of the composition, and preferably between 1% and 30% by weight relative to the total weight of the composition.

The composition according to the invention is preferably aqueous. In this case, the composition preferably comprises from 30% to 99% by weight of water, better still from 40% to 95% by weight of water and even better still from 50% to 90% by weight of water relative to the total weight of the composition.

Method or Treating Keratin Fibers

The invention also relates to a method for treating human keratin fibres, especially a method for dyeing and/or bleaching keratin fibers, which includes applying on said fibres a composition according to any of the preceding claims.

After a leave-on time of from one minute to one hour and preferably from 5 minutes to 30 minutes, the human keratin fibres are rinsed with water, and optionally washed with a shampoo and then rinsed with water.

The invention also relates to a process for dyeing keratin materials, comprising applying a ready to use composition resulting from the mixture of:
 (a) a composition (A) comprising at least an alkaline agent and optionally at least one oxidation dye precursor and/or at least one direct dye,
 (b) a composition (B) comprising at least one oxidizing agent,
 at least one of composition A and B comprising:
  at least one non ionic surfactant,
  at least one non associative polymer chosen from amphoteric polymers, cationic polymers and mixture thereof,
  at least one fatty substance other than fatty acids and
  at least one neutralized fatty acid,
  where the amount of fatty substance other than fatty acids in the ready to use composition is at least 10% by weight relative to the total weight of the composition and the amount of at least one neutralized fatty acid in the ready to use composition is at least 0.6% relative to the total weight of the composition.

According to a preferred embodiment, compositions A and B are extemporaneously mixed at the time of use and the mixture is applied to wet or dry keratin fibres.

In this variant, the weight ratio of the amounts of compositions A and B ranges from 0.1 to 10 and preferably from 0.3 to 3.

After a leave-on time of from one minute to one hour and preferably from 5 minutes to 30 minutes, the human keratin fibres are rinsed with water, and optionally washed with a shampoo and then rinsed with water.

The temperature during the process is conventionally between room temperature (from 15 to 25° C.) and 80° C. and preferably between room temperature and 60° C.

The examples that follow serve to illustrate the invention without, however, being limiting in nature.

EXAMPLES

The following compositions are prepared (the amounts are expressed in g % of active material):

Example 1

| Composition | A | A' |
|---|---|---|
| 1-BETA-HYDROXYETHYLOXY-2,4-DIAMINO-BENZENE DICHLORHYDRATE | 0.31 | 0.35 |
| SULFATE DE N,N-BIS(2-HYDROXYETHYL)-P-PHENYLENEDIAMINE, 1 H2O | 0.28 | 0.322 |
| 1,3-DIHYDROXYBENZENE (RESORCINOL) | 1.66 | 1.909 |
| 1-HYDROXY-3-AMINO-BENZENE | 0.14 | 0.161 |
| 1,4-DIAMINO-BENZENE | 2 | 2 |
| Coconut oil | 0.1 | 0.1 |
| Mineral oil | 11.5 | 11.5 |
| Sweet almond oil | 0.1 | 0.1 |
| Olive oil | 0.1 | 0.1 |
| Hexadimethrine chloride (Mexomere PO, Chimex) | 0.3 | 0.3 |
| Polyquaternium-6 (Merquat 100 from Nalco) | 0.4 | 0.4 |
| Cetylstearyl alcohol (C16/C18 50/50) | 20.5 | 20.5 |
| Cetylhydroxyethylcellulose (Natrosol Plus Grade 330 CS ®) | 0.03 | 0.03 |
| Oxyethylenated (12 EO) lauryl alcohol | 1.8 | 1.8 |
| Oxyethylenated (4 EO) lauryl alcohol | 3.6 | 3.6 |
| Oxyethylenated (20 EO) oleyl alcohol | 1.8 | 1.8 |
| Oxyethylenated (4EO) sorbitan monolaurate | 0.75 | 0.75 |
| Stearic acid | 1.75 | 2 |
| EDTA | 0.2 | 0.2 |
| Monoethanolamine | 3.3 | 3.4 |
| Ammonium hydroxide | 2.88 | 2.88 |
| Sodium metabisulfite | 0.5 | 0.5 |
| Ascorbic acid | 0.25 | 0.25 |
| Water | qs 100 | Qs 100 |

| Composition B | weight % |
|---|---|
| TRIDECETH-2 CARBOXAMIDE MEA | 0.85 |
| CETEARYL ALCOHOL (and) CETEARETH-25 (80/20) | 2.85 |
| Glycerol | 0.5 |
| Disodium tin hexahydroxide | 0.04 |
| Hydrogen peroxide | 6 |
| Tetrasodium pyrophosphate | 0.02 |
| Diethylenetriamine pentaacetic acid, pentasodium salt | 0.06 |
| Phosphoric acid | qs pH 2.2 |
| Water | qs 100 |

At the time of use, compositions A and A' are each mixed with composition B in a weight ratio 1/1.5.

The resulting mixtures do not have unpleasant odours. They are applied for 30 minutes at ambient temperature to brown hair.

The hair is then rinsed, washed with a standard shampoo and dried.

An intense and sparingly selective color is obtained on the hair.

Example 2

The following compositions are prepared (the amounts are expressed in g % of active material):

| | A" |
|---|---|
| 1-BETA-HYDROXYETHYLOXY-2,4-DIAMINO-BENZENE DICHLORHYDRATE | 0.25 |
| SULFATE DE N,N-BIS(2-HYDROXYETHYL)-P-PHENYLENEDIAMINE, 1 H2O | 0.22 |
| 1,3-DIHYDROXYBENZENE (RESORCINOL) | 1.33 |
| 1-HYDROXY-3-AMINO-BENZENE | 0.11 |
| 1,4-DIAMINO-BENZENE | 1.6 |
| Mineral oil | 6 |
| Olive oil | 0.1 |
| Polyquaternium-22 (Merquat 280 from Nalco) | 0.61 |
| Cetylstearyl alcohol (C16/C18 50/50) | 17 |
| Cetylhydroxyethylcellulose (Natrosol Plus Grade 330 CS ®) | 0.05 |
| Oxyethylenated (12 EO) lauryl alcohol | 1.5 |
| Oxyethylenated (4 EO) lauryl alcohol | 3 |
| Oxyethylenated (20 EO) oleyl alcohol | 1.5 |
| Oxyethylenated (4EO) sorbitan monolaurate | 0.25 |
| Stearic acid | 0.3 |
| EDTA | 0.2 |
| Monoethanolamine | 2.6 |
| Ammonium hydroxide | 2.06 |
| Sodium metabisulfite | 0.5 |
| Ascorbic acid | 0.25 |
| Water | qs 100 |

*am: active material

At the time of use, compositions A" and composition B of example 1 are mixed in a weight ratio 1/1.

The resulting mixtures do not have unpleasant odours. They are applied for 30 minutes at ambient temperature to brown hair.

The hair is then rinsed, washed with a standard shampoo and dried.

An intense and sparingly selective color is obtained on the hair.

The invention claimed is:

1. A composition for dyeing and/or bleaching human keratin fibers comprising:
   a) at least 0.15% of at least one neutralized fatty acid,
   b) at least one non ionic surfactant,
   c) at least one non associative polymer chosen from amphoteric polymers, cationic polymers and mixture thereof,
   d) at least 10% by weight relative to the total weight of the composition, of at least one fatty substance other than fatty acids, wherein the fatty substances other than fatty acids are chosen from C6-C16 hydrocarbons, hydrocarbons comprising more than 16 carbon atoms, non-silicone oils of animal origin, triglycerides of plant or synthetic origin and mixtures thereof, and fatty alcohols which are solid at room temperature and at atmospheric pressure,
   e) at least one oxidizing agent,
   f) at least an alkaline agent, and g) optionally at least oxidation one dye precursor and/or at least one direct dye.

2. The composition according to claim 1, in which the non associative polymer is chosen from:
cationic cyclopolymers of alkyldiallylamine or of dialkyldiallylammonium, hexadimethrine chloride and mixtures thereof,
amphoteric polymers chosen from polymers consisting of units derived from monomers (i) of (meth)acrylamide type, (ii) of (meth)acrylamidoalkyltrialkylammonium type and (iii) of (meth)acrylic acid type, copolymers based on (meth)acrylic acid and on a dialkyldiallylammonium salt,
and mixtures thereof.

3. The composition according to claim 1, in which the non associative polymer is present in an amount of between 0.01% and 5% by weight relative to the composition.

4. The composition according to claim 1, in which the neutralized fatty acids are chosen from salts of $C_{10}$ to $C_{24}$ fatty acids.

5. The composition according to claim 1, in which the neutralized fatty acids are chosen from salts of organic bases, and $C_{12}$-$C_{18}$ fatty acids.

6. The composition according to claim 1, comprising at least 0.2% of at least one neutralized fatty acid relative to the total weight of the composition.

7. The composition according to claim 1, in which the non ionic surfactants are chosen from oxyalkylenated non ionic surfactants.

8. The composition according to claim 1, in which the non ionic surfactants are chosen from oxyethylenated $C_8$-$C_{30}$ alcohols comprising from 1 to 100 mol of ethylene oxide.

9. The composition according to claim 1, in which the amount of non ionic surfactants ranges from 0.1 to 20%, by weight, relative to the total weight of the composition.

10. The composition according to claim 1, comprising at least one fatty substance other than fatty acids that is liquid at room temperature and at atmospheric pressure, and at least one fatty alcohol which is solid at room temperature and at atmospheric pressure.

11. The composition according to claim 1, comprising at least 12% by weight of fatty substances, relative to the total weight of the composition.

12. The composition according to claim 1, where the alkaline agent is chosen from alkanolamines.

13. The composition according to claim 1, containing at least an oxidation dye precursor.

14. The composition according to claim 1, containing at least one associative polymer.

15. The composition according to claim 14, in which the associative polymer is chosen from nonionic associative polymers.

16. The composition according to claim 2, wherein the non associative polymer is chosen from copolymers of (meth)acrylic acid and of dimethyldiallylammonium chloride.

17. The composition according to claim 5, wherein the neutralized fatty acids are chosen from salts of alkanolamines and $C_{12}$-$C_{18}$ fatty acids.

18. The composition according to claim 17, wherein the neutralized fatty acids are chosen from salts of monoethanolamine and $C_{12}$-$C_{18}$ fatty acids.

19. The composition according to claim 18, wherein the neutralized fatty acids are chosen from a salt of monoethanolamine and stearic acid.

* * * * *